(12) United States Patent
Harmon

(10) Patent No.: US 6,390,968 B1
(45) Date of Patent: May 21, 2002

(54) CERVICAL APPLICATOR FOR HIGH DOSE RADIATION BRACHYTHERAPY

(75) Inventor: Michael Harmon, Charleston, WV (US)

(73) Assignee: Paxton Equities, LLC, Charleston, WV (US)

( * ) Notice: Subject to any disclaimer, the term of this patent is extended or adjusted under 35 U.S.C. 154(b) by 69 days.

(21) Appl. No.: 09/588,697

(22) Filed: Jun. 7, 2000

(51) Int. Cl.[7] ............................. A61N 5/00; A61M 31/00
(52) U.S. Cl. ............................................ 600/6; 604/515
(58) Field of Search ................................ 600/3, 6, 2, 8, 600/7; 604/101.04, 515

(56) References Cited

U.S. PATENT DOCUMENTS

| | | | |
|---|---|---|---|
| 3,872,856 A | * | 3/1975 | Clayton .................. 600/6 |
| 4,292,960 A | | 10/1981 | Paglione |
| 4,554,909 A | | 11/1985 | Pino y Torres |
| 5,012,357 A | | 4/1991 | Schoeppel et al. |
| 5,104,377 A | | 4/1992 | Levine |
| 5,342,283 A | | 8/1994 | Good |
| 5,562,594 A | | 10/1996 | Weeks |
| 5,913,813 A | | 6/1999 | Williams et al. |
| 5,924,973 A | * | 7/1999 | Weinberger ............. 600/3 |
| 5,931,774 A | | 8/1999 | Williams et al. |

* cited by examiner

Primary Examiner—Eric F. Winakur
Assistant Examiner—Nikita R Veniaminov
(74) Attorney, Agent, or Firm—Cahn & Samuels, LLP

(57) ABSTRACT

A modified Fletcher-Suit tandem tube applicator includes a balloon which can be inflated to both positionally secure the applicator within the vaginal canal and to distend the confronting vaginal wall thereby increasing the distance of such tissue from the radioactive source contained in the tandem tube of applicator and correspondingly reducing radiation damage to nearby tissues and organs such as the rectum and bladder.

11 Claims, 1 Drawing Sheet

CERVICAL APPLICATOR FOR HIGH DOSE RADIATION BRACHYTHERAPY

BACKGROUND OF THE INVENTION

1. Field of the Invention

This invention relates to a modified Fletcher-Suit afterloading cervical applicator for use in brachytherapy. The invention includes a tandem and colpastat tube arrangement permitting introduction of radio-emissive material to intracervical tissues where the tubes are combined with at least one balloon that is inflatable in situ with a radiation attenuating fluid to positionally stabilize the applicator in the patient and provide selective shielding during high dose rate brachytherapy.

2. Description of the Art

Since shortly after the Curies' discovered radioactivity, radiotherapy has been used in connection with treatment of proliferative tissues and, particularly, in connection with cancer treatments and other oncological procedures. The two major categories of radiotherapy are teletherapy and brachytherapy. Teletherapy utilizes an external radiation source generally directed to a select region of the body to destroy cancer cells. Brachytherapy involves directly implanting/embedding a radioactive source within or proximate to a target cancerous mass for localized exposure.

Numerous medical devices and adjuncts have been developed for cervical cancer brachytherapy. An important early development was the Fletcher-Suit cervical applicator. The Fletcher (standard shielded) applicator provided a technique for intracervical/intrauterine introduction of a radioactive source. The traditional Fletcher applicator is employed in low dose therapies and comprises three hollow, metal tubes. The two, flanking "colpastat" tubes provide for intravaginal positioning and the medially disposed intrauterine "tandem" tube is adapted to traverse the vaginal canal and project into the cervix. The conventional Fletcher-Suit system design suffers from a known in situ positioning problem attributed, in part, to the absence of a secure connection between the colpastat tubes and the tandem tube.

Variations of the Fletcher-Suit applicator for intrauterine brachytherapy have evolved from its original form. For example, in Weeks U.S. Pat. No. 5,562,594 a modified Fletcher tandem device providing shielding for protection of untargeted tissues is described. The Weeks applicator features an inflatable lumen applicator with one embodiment incorporating dual inflatable balloons for delivery and placement of radioactive fluid for temporary brachytherapy. The stated purpose of the Weeks applicator is to reduce the dose of radiation applied to internal organs, such as the rectum, without the need to decrease the dose targeted at the tumor-bearing areas. Because Weeks contains a relatively comprehensive discussion of the physics and anatomy associated with intracervical brachytherapy using a Fletcher tandem, its content is incorporated herein by reference.

Schoppel et al., in U.S. Pat. No. 5,012,357, discloses an intracavity brachytherapy applicator permitting "afterloading" shielding particularly useful in CT scanning procedures. Morrison, in U.S. Pat. Nos. 4,244,357 and 5,947,891, discloses a dual tube brachytherapy delivery system including at least one hollow tube (an intravaginal tube) having an inner end adapted for insertion into the vaginal cavity, and a second hollow tube (an intracervical tube) having an inner end adapted for insertion into the cervix and the uterus. Finally, by way of exemplary prior art technologies, Weinberger, in U.S. Pat. No. 5,924,973, describes an applicator incorporating a balloon catheter in fluid communication with an indiflator for inflation with a radioactive fluid.

Brachytherapy is divided into two major classifications, low dose rate (LDR) and high dose rate (HDR). Low dose rate treatments typically involve dose rates of 40 to 60 centigray per hour and more typically about 55 centigray/hr. High dose brachytherapy, on the other hand, contemplates significantly higher rates of dose delivery (up to 1000 centigray per minute) and not uncommonly in the range of hundreds of centigray in minutes. High dose and low dose brachytherapy are generally believed to be of substantially equal efficacy oncologically, albeit that HDR is generally recognized to provide significant delivery efficiencies over a low dose alternative. Notwithstanding significantly enhanced radiation delivery efficiencies, many hospitals and medical treatment providers have opted not to use HDR treatments due to reportedly higher incidences of complications of which the most frequent complications arise from radiation damage to healthy tissues and organs proximate to the implanted/embedded radiation source. The risk of such complications resulting from HDR treatment is believed to have steered some healthcare professionals to conventional LDR techniques and/or use of hybrid LDR/HDR delivery schemes providing radiation delivery at a substantially augmented rate relative to LDR but at a substantially reduced rate from HDR. Thus, while reportedly reducing the risk of complications, such hybrid treatments also represent a corresponding loss of delivery efficiencies.

In brachytherapy associated with treatment of cervical cancer, LDR treatment minimizes collateral and undesirable damage to healthy tissues, e.g. the bladder and rectum, but achieves its therapeutic effect only by subjecting a patient to prolonged periods of immobilization during exposure. Thus, it is not unusual for LDR procedures, particularly in the treatment of cervical cancer, to require hospitalization for days. Furthermore, prolonged procedures result in patient aggravation, inconvenience, and discomfort while also significantly increasing treatment costs attributable to extended hospitalization, all without any significant augmentation in efficacy.

In contradistinction, HDR intra-cervical brachytherapy provides an efficient alternate therapeutic option. HDR may significantly reduce, from days to minutes, the duration of exposure and patient immobilization. Thus, HDR eliminates the need for prolonged hospitalization and reduces patient inconvenience and discomfort without a loss of therapeutic efficacy. In short, reliance on HDR provides significant advantages in healthcare delivery efficiency, minimizes patient discomfort, and even permits outpatient treatment.

Recognizing both the value and potential harm from HDR, healthcare providers have turned to various shielding techniques to minimize undesirable collateral tissue damage in HDR brachytherapy procedures. However, such shielding is difficult to use and difficult to position in situ. Even minor displacement of selective radiation attenuating shielding in situ defeats the benefit provided thereby. If displaced, the shielding not only fails to diminish exposure of healthy tissues but also may obstruct exposure of targeted proliferative tissues. Moreover, the use of effective shielding is increasingly difficult where the applicator embodies complicated structures that either interfere with or are interfered with by the shielding.

Conventional shielding material, e.g., metal, barium fluids, etc. are opaque to radiation which serves admirably to attenuate impinging radiation. However, the very radiation attenuating excellence also obstructs efficient monitoring of the general area by electromagnetic-based instrumentation, for example, tomographs, magnetic resonance imagers, etc. and the more traditional x-rays and fluoroscopes. Finally, conventional shielding does not contribute to stable positioning of the applicator during treatment in conjunction with its function to shield healthy tissue from exposure.

SUMMARY OF THE INVENTION

It is, therefore, an object of the present invention to address and overcome problems of the prior art brachytherapy apparatus and methods. It is another object of this invention to provide a highly efficient and efficacious intracervical and intervaginal brachytherapy delivery system.

Another object of this invention is to provide selective attenuation of radiation emitted from an internally disposed radiation source without reducing dose rate exposure to a selected target.

A further object of the invention provides an applicator for intra-cervical HDR brachytherapy that attenuates radiation exposure of proximate healthy, non-target tissue.

It is still another object of the invention to improve intra-cervical brachytherapy delivery while minimizing patient discomfort and inconvenience.

Still another object of the invention is to maintain therapeutic efficacy and maximize delivery efficiencies of intracervical and transvaginal brachytherapy.

A more particular object of this invention is to provide unattenuated delivery of high dose rate radiation to a proliferative tissue/tumor zone by intra-cervical/transvaginal brachytherapy while providing a radiation-attenuating prophylactic for proximate tissues such as the bladder and rectum during intra-cervical HDR brachytherapy. A final stated, but only one of additional numerous objects of the invention, is to provide a radiation attenuating apparatus and method that is at once effective, inexpensive and easily deployed in for HDR brachytherapy procedures.

These and other objects are satisfied by a modified Fletcher-Suit applicator for delivery of an irradiation source used in brachytherapy comprising:

an elongated, rigid tandem tube having a proximal end including an opening and a closed distal end where the tandem tube has a sufficient length to project transvaginally and a select distance into the cervix, said tandem tube defining a hollow bore and permits selectively removable insertion of a radioactive source from said proximal opening to the distal end;

a colpastat tube;

rigid connecting means for affixedly connecting the tandem and colpastat tubes at a select distance therebetween;

inflatable balloon means mounted on a select one of said tubes for positionally securing said applicator within a patient's vaginal canal and for providing attenuation of radioactive emissions from the radioactive source to tissues proximate to the balloon; and fluid communication means for communicating radiation-attenuating fluid between a reservoir and said balloon and cause the inflation and deflation thereof.

The foregoing and other objects are satisfied by a brachytherapy method comprising:

inserting an applicator transvaginally where the applicator includes a rigid tube of a length sufficient to project intracervically and the tube has affixed thereto an inflatable balloon where the balloon is positionable within the vaginal canal;

inflating the balloon with a radiation attenuating fluid where the balloon expands against the wall of the vaginal canal;

urging the vaginal canal wall away from the tube, and inserting a radioactive sample into the applicator.

In short, the present invention provides a cervical applicator for brachytherapy which is capable of attenuating the dose of radiation exposure of selected tissues in the proximity of the target tissue and also contemplates a method of employing a cervical applicator for brachytherapy and a method for attenuating radiation exposure to untargeted tissues during brachytherapy.

According to one aspect of the present invention, a cervical applicator for use in intracervical brachytherapy includes a tube assembly for insertion through the vaginal canal and into the cervix. The tube assembly comprises a transvaginal portion connected to an intracervical tube portion with at least one inflatable balloon mounted proximally to the distal end of the intracervical portion of one of the tubes. Following introduction and preliminary positioning through the external os of the intracervical tube portion, the balloon is inflated with a radiation attenuating fluid from an external reservoir in fluid communication with the balloon. As the balloon inflates, it expands and upon reaching a sufficient inflation pressure, presses against and displaces the vaginal wall from the tubes.

As in the case of a typical Fletcher-Suit applicator, the invention uses the balloon arrangement to provide intravaginal positional stabilization and displacement of vaginal tissues. The particular balloon arrangement, however, may vary. For example, the balloon may itself comprise an annular member physically attached to and surrounding the transvaginal/intracervical tube of the applicator. Alternatively, the balloon may be mounted on a supporting platform mounted on the tube or may be attached or affixed to the applicator tube without surrounding the tube.

In general terms, the invention herein contemplates a brachytherapy method and adjunct calling for the transvaginal insertion of a cervical applicator providing a projecting tube portion for intra-cervical disposition and a combination radiation attenuating, tube-position-stabilizing balloon for in situ inflation. Upon inflation, the selected position of the applicator is thereby fixed relative to the vaginal canal and uterine cavity by, at minimum, an interference fit with the vaginal wall and cervix, and more desirably, by pressing with sufficient force on the vaginal wall to induce displacement thereof from the tube and to provide selected radiation attenuating shielding of nearby healthy tissues. Once the health care provider is satisfied with the physical disposition of the device and shielding the radiation source may be introduced in the conventional manner through the tube passage and to the proximal tip of the tube which, ideally has been positioned at or near the target tissue/mass. As a consequence, the balloon protects internal tissues/organs adjoining the vagina by increasing the distance thereof the radioactive source as well as providing attenuating shielding to significantly decreasing radiation exposure during HDR of the organ/tissue.

The foregoing and other objects and advantages will appear from the description to follow. In short, the invention herein is directed an original or retrofitted intracervical applicator for HDR brachytherapy providing maximum radiation delivery efficiencies to targeted tissues while mitigating adverse effects to such exposure of proximate healthy tissues. The invention contemplates both apparatus dedicated to its employ and converting existing structures using off-the-shelf basic components already available to healthcare delivery professionals.

For definitional purposes and as applicable, the inner tube end is referred to as "distal" and the end accessible for manipulation by the healthcare provider is referred to as "proximal" (typically projecting external of the patient's body).

As used herein "connected" includes physical, whether direct or indirect, permanently affixed or adjustably mounted, as for example, the balloon on the transvaginal tube portion of the apparatus or the case of two tubes in a tandem. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Given the following detailed description, it should become apparent to the person having ordinary skill in the art that the invention herein provides a brachytherapy adjunct and method designed for use in HDR procedures thereby permitting exploitation of the significantly augmented delivery efficiencies provided by HDR while mitigating the complications arising from its use.

DESCRIPTION OF THE ILLUSTRATED EMBODIMENTS

Figure 1:
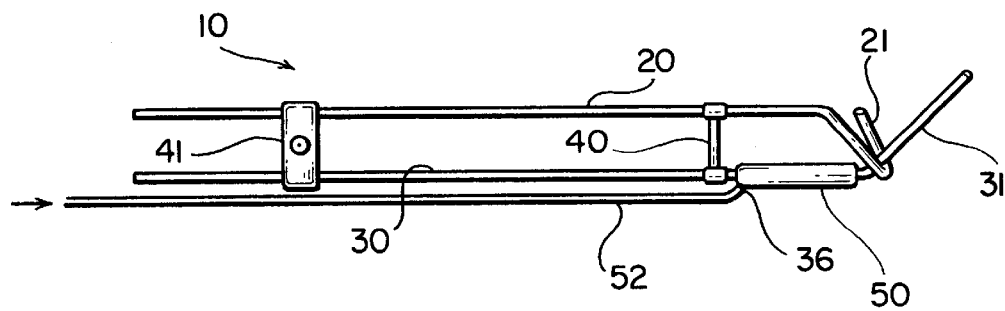
FIG. 1 is a side elevation of an embodiment of a cervical applicator according to the present invention with a balloon of the applicator in a deflated state.
Figure 2:
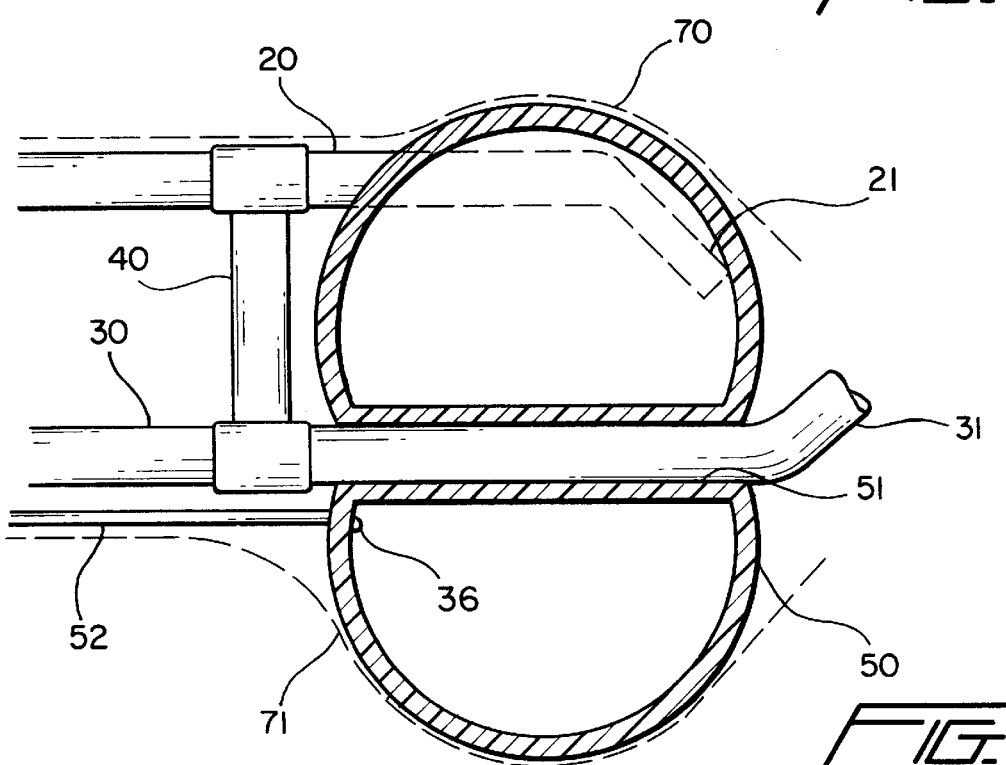
FIG. 2 is an enlarged cross-sectional view of the balloon of FIG. 1 in an inflated state.
Figure 3:
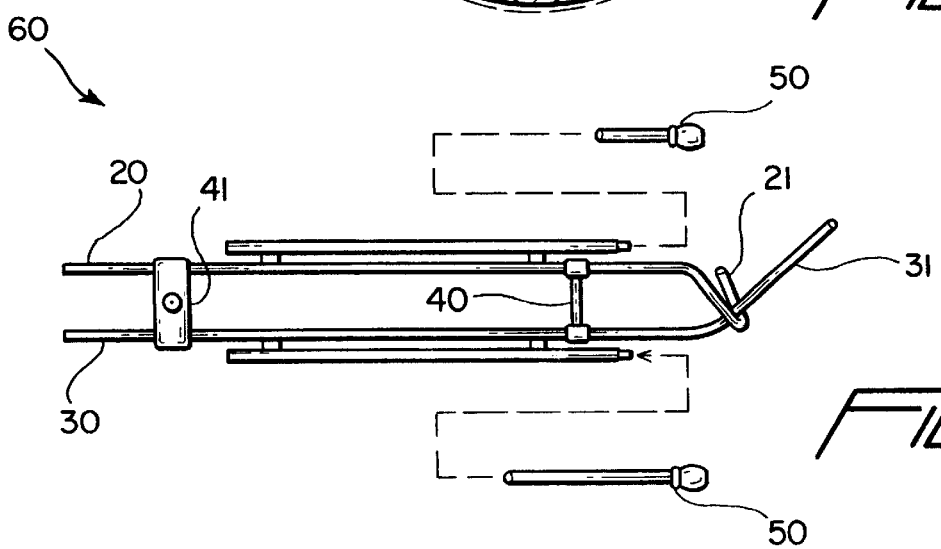
FIG. 3 is a side elevation of second embodiment of a cervical applicator.

Two embodiments of a Fletcher-Suit type cervical applicator according to the present invention are now described making reference to the accompanying drawings. FIGS. 1 and 2 illustrate a first embodiment of a cervical applicator 10 and FIG. 3 represents an alternative embodiment, applicator 60. The applicator 10 of FIG. 1 comprises, as its major components intravaginal tube 20, a distal, angled cervix ring 21, a hollow, transvaginal-intracervical tube 30 including a intracervical projection portion 31, a bridge 40, a bridge 41, an inflatable balloon 50, and a fluid channel tube 52. In more detail, the colpastat-intravaginal tube 20 is formed from an appropriate rigid, medical grade material such as surgical stainless steel, titanium, carbonate polymers, or other suitable materials providing adequate strength, rigidity, and sterilizable surfaces. The tube 20, preferably having a circular cross-section, may be solid or hollow. In the hollow form, the tube 20 effectively, qualifies as a second tandem tube, thereby providing a dual tandem arrangement where the internal channel permits introduction of a selected element, such as instrumentation, e.g., a thermometer or a radiation dose/rate monitor. In more pernicious cases, the hollow tube 20 allows for introduction of a radiation source, e.g., a capsule/pellet of radium, cesium, or an alternate source of ionizing, to the distal end in proximity to tumorous tissues. The present invention contemplates after-loading to protect healthcare delivery professionals. In other words only after the apparatus 10 is selectively positioned within the patient, is the radioactive source removed from isolation, as described, for example in U.S. Pat. No. 4,969,863 to van't Hooft et al.

The cervical ring 21 located on the distal end of the tube 20, preferably is formed integrally with the tube 20 but may comprise an affixable attachment composed from the same or a different material. For example, the ring 21 may be formed from a rigid polymer that provides an annulus of greater diameter than that of the tube 20. In the case of a multi-piece arrangement, it is critical that the ring 21 be securely attachable, by a compression fitting or the like, to the tube 20 in a non-displaceable manner, at least while the applicator is utilized in situ. Such designs and variations of the cervical ring 21 and its attachment to the intravaginal tube 20 are well-known and within the skill and knowledge of cervical applicator designers.

The transvaginal/intracervical tandem tube 30, preferably comprises a hollow, rigid, tube having a length sufficient to extend through the entire vaginal canal, through the exterior os, the cervix, the interior os, and project a select distance (determined by the particular physiology of the patient) into the uterine cavity. As in the case of the tube 20, the tube 30 may be formed from surgical stainless steel and the like. The distal end of the tube incorporates the intracervical portion 31 which typically is angled from the tube to facilitate insertion of the intra-uterine portion 31 through the cervix. The selection of the angle is dictated by physiology and the requirement to allow for translation of a radioactive source (typically solid) through the entire tube length to the distal tip of portion 31.

As illustrated in FIG. 1 tandem tube 30 and colpastat tube 20 are maintained in a space-apart relation by spacing bridges 40 and 41. These bridges serve to maintain separation of tubes, particularly during introduction of the applicator 10. As illustrated the bridge 40 is fixed and the bridge 41 is adjustable. The bridge 40 may be formed integrally with the tube 20 or may comprise a bracket of selectable length that is affixedly attachable to both of the tubes 20 and 30 proximally of the ring 21. Any number of well known structural adjuncts may be employed to facilitate adjustablilty of the bridge 41 such as, for example, clamps that journal the tubes while permitting the separation distance to be varied. The ultimate setting for adjustable bridge 41 is made by the healthcare delivery professional based on the particular requirements of the patient being treated.

Unlike a conventional Fletcher-Suit applicator which typically relies on an interference fit established between the anterior and posterior walls of the vaginal canal and the colpastat tubes, the present invention relies on the cooperation of the single colpastat tube and an inflatable balloon 50 for in situ positioning. The inflatable balloon 50 is positioned along the intracervical tube 30 proximate to both portion 31 and the cervical ring 21 and distally of the fixed bridge 40. The balloon 50 is connected to and in fluid communication with a fluid introduction tube 52 used for fluid introduction to and withdrawal of fluid from the balloon 50. The fluid introduction tube 52 may be rigid but preferably is flexible and possesses sufficient hoop strength to avoid collapse during use.

Compliant balloons meeting the requirements of the invention may be composed of any suitable medical grade elastomer that provides physical strength and elasticity characteristics required to practice the invention. It is also important that the balloon material possess adequate resistance to radioactive decomposition and, critically, in connection with the invention, be compatible with radiation attenuating fluids. Several materials meet these requirements as for example, silicon, vinyl, urethane, latex, etc. In other words, compositions conventionally used for inflatable balloons for medical purposes are generally suitable. In actual use, the balloon 50 is of the kind used in enumerate procedures such as the FLEX-CUFF non-latex, silicone elastomer, retention cuff manufactured by EZEM, Inc. of Westbury, N.Y. (Cata. No. 8816). The balloon 50 was obtained by truncating a conventional retention tip used for administering a barium enema in radiographic procedures and slipping the truncated portion, including the balloon 50, over the intracervical tube 30. The truncated retention cuff has sufficient strength and elasticity to meet the operational requirements of the invention and permits mounting proximate to the cervical ring 21. Another structure meeting the functional criteria for the balloon 50 is a Bardex® balloon commonly used with a barium enema rectal catheter.

In order to meet the operational objectives of the invention, the balloon should possess adequate strength to physically displace muscular tissues (e.g., the vaginal walls), upon inflation without risk of rupture. Moreover, the balloon 50 preferably is affixed directly to the tandem tube 30 with an appropriate bonding adhesive such as Loctite or other cyanoacrylates in a manner to provide adequate adhesion and to minimize exposure thereof in situ. The balloon 50 is deployed in a deflated state and employed in an inflated state. In a deflated state, the cross-sectional dimension of the balloon 50 is selected so as not to interfere with insertion of the applicator 10 and, upon inflation, the balloon expands radially outwardly from the tube to impinge on the vaginal cavity walls. As the balloon 50 is filled with the attenuating fluid of choice, it expands radially outwardly under pressure to confront the juxtaposed vaginal cavity wall portion. By retaining the inflating pressure within the balloon, the outer wall of the balloon retains its expanded position. The balloon also includes a fluid communication port/channel 36 formed in its wall. The port 36 is connected to a reservoir of radiation attenuating fluid (not illustrated) via the tube 52, to communicate the fluid, under pressure, to and from the balloon 50. As indicated above, water is the preferred balloon inflation fluid for practice of the invention. Water provides good radiation attenuation and is also transparent/semi-transparent to certain radiation forms thereby permitting monitoring during brachytherapy. Other fluids, such as barium salt solutions provide excellent radiation attenuation but also comprise an essentially radio-opaque barrier which obscures monitoring during the HDR procedures contemplated herein.

The invention also contemplates utilizing more than one balloon 50 on one or both of tubes 20 and 30. In its inflated state, the balloon 50 preferably has a size such to provide an interference fit to securely position applicator 10 during brachytherapy procedures and to displace the vaginal wall. The balloon 50 may incorporate various inflated configurations and may even be segmented in accordance with well known techniques, to provide differing degrees of attenuation along selected profiles. For example, if the primary internal organ to be protected against radiation is the rectum, the balloon 50 may be shaped to expand more towards the posterior wall 71 of the vagina than towards the anterior wall 70. Consequently, the balloon 50 may define any number of inflated configurations so long as it is able it to push against the vaginal wall and physically dilate the cavity in a desired manner.

Positioning of the balloon 50 on the tandem tube is dictated by the intended use. If the caregiver's objective is to maximize protection of the rectum, the balloon is best located on the tandem tube 30 because it is closer to the rectum. Thus, the balloon 50 pushes against the posterior wall 71 of the vagina when in an inflated state. If it is desired to primarily protect the bladder from radiation, the balloon 50 may instead be installed on the intravaginal tube 20, which is closer to the bladder to push against the anterior wall 70 of the vagina when in an inflated state. Where both areas are to be protected, as noted above, the invention contemplates a balloon may be installed on each of tubes 20 and 30. In either case, when deflated, the outer annular wall of balloon 50 loosely surrounds the tube so as to generally match the narrow crosssectional profile of the tube.

Operation

The cervical applicator 10 can be used in much the same way as a conventional cervical applicator. Before any radioactive samples have been loaded into it, the applicator 10 is inserted into a patient's body, with the ring 21 of the intravaginal tube 20 located in the vaginal vault in the vicinity of the cervix with the intracervical portion 31 of the intracervical tube 30 extending into the cervix. The balloon 50 is connected to a source of inflating fluid and inflated, preferably by hand, until it presses the posterior and/or anterior wall of the vagina away from the tube 20 to increase the distance of the rectum and/or the bladder from the ring 21. A radioactive sample is then introduced into tube 30, and is resident at the distal end of the tube for a predetermined length of time in accordance with the dose to be administered. Inflation of the balloon 50 is maintained throughout administration of the dose. At the end of the predetermined length of time, the radioactive sample is removed from the applicator 10, the balloon 50 is deflated by allowing the inflating fluid to flow out through the tube 52, and the applicator 10 withdrawn from the patient's body. The balloon 50 can then be discarded, while the tubes 20, 30 and other portions of the applicator 10 can be sterilized for reuse.

As referred to above, the balloon 50 is inflated in situ to a degree sufficient to engage and distend one or both of the anterior wall 70 and the posterior vaginal wall 71 It should be readily apparent that expanding the anterior wall 70 of the balloon 50 increases the distance of the bladder from the radiation source containing tandem tube 30. Correspondingly, expanding the posterior wall 71 increases the distance of the rectum from the tube.

Clinical evaluation of cervical applicators according to the foregoing have borne out the efficacy of the invention. Pelvimetric radiographs were obtained with the balloon 50 deflated and inflated, and computer dosimetry was performed to compare rectal doses for the two conditions, with all other factors other than the state of inflation unchanged. The rectal dose with the balloon 50 inflated was decreased in nearly every case compared to the does when the balloon 50 was deflated, with the decrease in dose of up to 67% and with an average decrease in the dose delivered to the rectum of 16%. This decrease in dose is highly significant, because it not only can decrease complications caused by treatment but can also improve cure rates by allowing higher doses to be delivered to tumor-bearing areas.

Referring briefly to FIG. 3, it illustrates an alternative embodiment of the invention. The cervical applicator 60 corresponds to a conventional Fletcher-Suit applicator in as much as it features a tandem tube flanked by a pair of colpastat tubes. In accordance with the description of the first embodiment of the present invention, the alternative embodiment may include a single balloon located on the tandem tube or may include multiple balloons. In the case of multiple balloons, there is no requirement that they be of identical shape or elasticity or even that both share a common fluid/fluid input tube or each have its own tube and own reservoir (particularly desirable where each balloon is connected to a dedicated fluid reservoir that may or may not contain a fluid possessing different attenuating properties). Moreover, the balloons, as described above may be attached directly to the tubes or may be attached to a carrier platform fixedly mounted to the tube(s).

Use of the applicator 60 corresponds to that of applicator 10, described above. After the applicator 60 has been inserted into a patient's body, one or more balloons is inflated to immobilize the applicator 60 in a desired location and orientation in the patient's body and to interfere with radioactive emissions to non-targeted tissues emanating from the after-loaded radioactive source.

Variations of the above-described apparatus and methods are intended to fall within the scope and spirit of the invention. For example, the intrauterine tube portion may include a separate portion adjustment inflatable balloon such as that disclosed in Levine U.S. Pat. No. 5,104,377 or incorporate, if desired, a dual balloon arrangement adapted from the disclosure of enemata devices disclosed in U.S. Pat. No. 4,019,515. In such an adaptation, the proximal balloon would be located near the distal end of the vaginal canal and the distal balloon would be located in the cervix. Further variations include the use of segmented balloons to permit even further selectivity of attenuating fluid to specific segments. For example, a fluid exhibiting a selected attenuating capacity could be selectively introduced into a selected balloon chamber/segment. One example of a co-spherical balloon, multi-channel arrangement is illustrated in the subcutaneously implantable, brachytherapy device described in Williams, et al, U.S. Pat. No. 5,913,813.

Given the foregoing, it should be apparent that the specifically described embodiments are illustrative and not intended to be limiting. Furthermore, variations and modifications to the invention should now be apparent to a person having ordinary skill in the art. These variations and modifications are intended to fall within the scope and spirit of the invention as defined by the following claims.

What is claimed is:

1. A cervical applicator for use in brachytherapy comprising:
    a rigid, intravaginal tube for receiving a radioactive sample therein and insertion into a patient's vagina;
    a hollow, rigid intracervical tube coupled to the intravaginal tube for receiving a radioactive sample therein and insertion into the patient's cervix;
    an inflatable balloon element mounted on an intravaginal portion of one of the tubes; and
    a fluid tube for communicating inflation fluid to the inflatable balloon element,
    where the balloon is inflatable with a radiation attenuating fluid to reduce the effective impinging radiation dose passing therethrough and to urge the tissues in contact with the inflated balloon away from the tubes; and
    wherein the intravaginal tube includes a ring adapted to seat against the exterior os at an end thereof surrounding the intracervical tube.

2. A cervical applicator for use in brachytherapy comprising:
    a rigid, intravaginal tube for receiving a radioactive sample therein and insertion into a patient's vagina;
    a hollow, rigid intracervical tube coupled to the intravaginal tube for receiving a radioactive sample therein and insertion into the patient's cervix;
    an inflatable balloon element mounted on an intravaginal portion of one of the tubes wherein the balloon is an inflatable, non-latex, silicone elastomer, retention colon cuff used for barium enemas; and
    a fluid tube for communicating inflation fluid to the inflatable balloon element,
    where the balloon is inflatable with a radiation attenuating fluid to reduce the effective impinging radiation dose passing therethrough and to urge the tissues in contact with the inflated balloon away from the tubes.

3. A cervical applicator as claimed in claim 2 including a first balloon catheter mounted on the intravaginal tube and a second balloon catheter mounted on the intracervical tube.

4. A cervical applicator as claimed in claim 3 including a first catheter support tube mounted on the intravaginal tube and receiving the first balloon catheter and a second catheter support tube mounted on the intracervical tube and receiving the second balloon catheter.

5. A modified Fletcher-Suit applicator for delivery of an irradiation source used in brachytherapy comprising:
    an elongated, rigid tandem tube having a proximal end including an opening and a closed distal end where the tandem tube has a sufficient length to project transvaginally and a select distance into the cervix, said tandem tube defining a hollow bore and permits selectively removable insertion of a radioactive source from said proximal opening to the distal end;
    a colpastat tube;
    rigid connecting means for affixedly connecting the tandem and colpastat tubes at a select distance therebetween;
    inflatable balloon means mounted on a select one of said tubes for positionally securing said applicator within a patient's vaginal canal and for providing attenuation of radioactive emissions from the radioactive source to tissues proximate to the balloon; and
    fluid communication means for communicating radiation attenuating fluid between a reservoir and said balloon and cause the inflation and deflation thereof.

6. The modified applicator of claim 5 where the balloon is affixed to the tandem tube with an adhesive.

7. The modified applicator of claim 6 where the colpastat tube includes a cervical ring.

8. The modified applicator of claim 5 where the rigid connecting means permits adjustment of the spacing between the tandem and colpastat tubes.

9. A brachytherapy method comprising:
    inserting an applicator transvaginally where the applicator includes a rigid tube of a length sufficient to project intracervically and the tube has affixed thereto an inflatable balloon where the balloon is positionable within the vaginal canal;
    positioning the balloon proximate to the os to expand the inflated balloon against the vaginal wall to displace the vaginal tissues proximate to the os and patient's rectum away from the radiation source;
    inflating the balloon with a radiation attenuating fluid where the balloon expands against the wall of the vaginal canal;
    urging the vaginal canal wall away from the tube, and inserting a radioactive sample into the applicator.

10. The method of claim 9 including expanding an anterior wall of the vaginal canal with the inflated balloon to displace the bladder from the radioactive sample.

11. A method of using a modified Fletcher-Suit applicator for delivery of an irradiation source used in brachytherapy comprising:

an elongated, rigid tandem tube having a proximal end including an opening and a closed distal end where the tandem tube has a sufficient length to project transvaginally and a select distance into the cervix, said tandem tube defining a hollow bore and permits selectively removable insertion of a radioactive source from said proximal opening to the distal end;

a colpastat tube;

rigid connecting means for affixedly connecting the tandem and colpastat tubes at a select distance therebetween;

inflatable balloon means mounted on a select one of said tubes for positionally securing said applicator within a patient's vaginal canal and for providing attenuation of radioactive emissions from the radioactive source to tissues proximate to the balloon; and fluid communication means for communicating radiation attenuating fluid between a reservoir and said balloon and cause the inflation and deflation thereof, comprising the step of distending an anterior wall of the patient's vagina with a first balloon and expanding a posterior wall of the patient's vagina with a second balloon.

* * * * *